(12) United States Patent
Popescu

(10) Patent No.: US 11,896,716 B2
(45) Date of Patent: Feb. 13, 2024

(54) METHOD FOR THE FORMULATION OF OIL-SOLUBLE SUBSTANCES, AND POWDERS OBTAINABLE THEREOF

(71) Applicant: ROQUETTE AMERICA, INC., Geneva, IL (US)

(72) Inventor: Carmen Popescu, Geneva, IL (US)

(73) Assignee: Roquette America, Inc., Geneva, IL (US)

( * ) Notice: Subject to any disclaimer, the term of this patent is extended or adjusted under 35 U.S.C. 154(b) by 284 days.

(21) Appl. No.: 16/759,925

(22) PCT Filed: Oct. 30, 2018

(86) PCT No.: PCT/US2018/058116
§ 371 (c)(1),
(2) Date: Apr. 28, 2020

(87) PCT Pub. No.: WO2019/089520
PCT Pub. Date: May 9, 2019

(65) Prior Publication Data
US 2021/0137790 A1  May 13, 2021

Related U.S. Application Data

(60) Provisional application No. 62/579,352, filed on Oct. 31, 2017.

(30) Foreign Application Priority Data

Nov. 10, 2017  (EP) .................................. 17201162

(51) Int. Cl.
| | | |
|---|---|---|
| A61K 9/16 | (2006.01) |
| A61K 9/20 | (2006.01) |
| A61K 31/00 | (2006.01) |
| A61K 31/01 | (2006.01) |
| A61K 31/015 | (2006.01) |
| A61K 31/045 | (2006.01) |
| A61K 31/05 | (2006.01) |
| A61K 31/07 | (2006.01) |
| A61K 31/122 | (2006.01) |
| A61K 31/17 | (2006.01) |
| A61K 31/21 | (2006.01) |
| A61K 31/355 | (2006.01) |
| A61K 45/00 | (2006.01) |
| A61K 45/06 | (2006.01) |
| A61K 47/36 | (2006.01) |
| A61K 47/44 | (2017.01) |
| B01J 13/04 | (2006.01) |
| B05B 5/00 | (2006.01) |
| A61J 3/02 | (2006.01) |
| A61J 3/06 | (2006.01) |
| A61J 3/07 | (2006.01) |
| A61J 3/10 | (2006.01) |
| A23D 9/05 | (2006.01) |
| A23D 7/005 | (2006.01) |
| A23D 9/007 | (2006.01) |

(52) U.S. Cl.
CPC .......... *A61K 9/1682* (2013.01); *A23D 7/0053* (2013.01); *A23D 9/007* (2013.01); *A23D 9/05* (2013.01); *A61J 3/02* (2013.01); *A61J 3/06* (2013.01); *A61J 3/07* (2013.01); *A61J 3/074* (2013.01); *A61J 3/10* (2013.01); *A61K 9/16* (2013.01); *A61K 9/167* (2013.01); *A61K 9/20* (2013.01); *A61K 9/2095* (2013.01); *A61K 31/00* (2013.01); *A61K 31/01* (2013.01); *A61K 31/015* (2013.01); *A61K 31/045* (2013.01); *A61K 31/05* (2013.01); *A61K 31/07* (2013.01); *A61K 31/122* (2013.01); *A61K 31/17* (2013.01); *A61K 31/21* (2013.01); *A61K 31/355* (2013.01); *A61K 45/00* (2013.01); *A61K 45/06* (2013.01); *A61K 47/36* (2013.01); *A61K 47/44* (2013.01); *B01J 13/043* (2013.01); *B05B 5/001* (2013.01)

(58) Field of Classification Search
None
See application file for complete search history.

(56) References Cited

U.S. PATENT DOCUMENTS

| | | | |
|---|---|---|---|
| 7,252,848 | B2 | 8/2007 | Gelin |
| 8,883,243 | B2 | 11/2014 | Freres |
| 8,939,388 | B1 | 1/2015 | Beetz et al. |
| 2002/0127303 | A1* | 9/2002 | Chen ........................ A23L 33/15 |
| | | | 426/89 |
| 2005/0048181 | A1* | 3/2005 | Gelin ...................... A23C 21/06 |
| | | | 426/534 |

(Continued)

FOREIGN PATENT DOCUMENTS

| | | |
|---|---|---|
| CN | 103082033 A | 5/2013 |
| WO | 2011039336 A1 | 4/2011 |

(Continued)

OTHER PUBLICATIONS

Leyva et al "Modeling Pharmaceutical Powder-Flow Performance Using Particle-Size Distribution Data", Pharmaceutical Technology, vol. 33(3), p. 1-6. (Year: 2009).*

(Continued)

*Primary Examiner* — Sin J Lee

(57) ABSTRACT

The invention relates to a new method for the formulation of oily substances, and to powders and solid dosage forms obtainable thereof. The process comprises a step of spray-drying of an oil-in-water emulsion comprising an octenyl succinate starch and a maltodextrin.

45 Claims, No Drawings

(56) References Cited

U.S. PATENT DOCUMENTS

| | | | |
|---|---|---|---|
| 2010/0196542 A1* | 8/2010 | Boursier | A23P 10/30 426/302 |
| 2012/0039970 A1* | 2/2012 | Kopsel | A23K 20/179 514/763 |
| 2015/0110924 A1 | 4/2015 | Bromley | |
| 2017/0130052 A1 | 5/2017 | Trotta et al. | |

FOREIGN PATENT DOCUMENTS

| | | |
|---|---|---|
| WO | 2014180827 A1 | 11/2014 |
| WO | 2016123224 A1 | 8/2016 |

OTHER PUBLICATIONS

Wang et al ("Quality analysis and microencapsulation of chili seed oil by spray drying with starch sodium octenylsuccinate and maltodextrin", Powder Technology, vol. 312 (2017), p. 294-298) (Year: 2017).*

The International Search Report and Written Opinion, dated Jan. 28, 2019, in the corresponding PCT Appl. No PCT/US2018/058116.

Regiane Victória de Barros Fernandes et al., "Gum arabic/starch/maltodextrin/inulin as wall materials on the microencapsulation of rosemary essential oil," Carbohydrate Polymers, vol. 101, Jan. 30, 2014, pp. 524-532.

\* cited by examiner

METHOD FOR THE FORMULATION OF OIL-SOLUBLE SUBSTANCES, AND POWDERS OBTAINABLE THEREOF

CROSS-REFERENCE TO RELATED APPLICATIONS

This application is a National Stage Application of PCT/US2018/058116 filed Oct. 30, 2018, which claims priority from U.S. Provisional Patent Application No. 62/579,352, filed on Oct. 31, 2017 and European Patent Application No. 17201162.9, filed on Nov. 10, 2017. The priority of said PCT, said U.S. Provisional Patent Application and European Patent Application are claimed. Each of the prior mentioned applications is hereby incorporated by reference herein in its entirety.

The invention relates to a new method for the formulation of oily substances, and to powders and solid dosage forms obtainable thereof. In particular, the method uses electrostatic spray-drying of an oil-in-water emulsion comprising specific starchy materials. The powder obtained is particularly suitable for the preparation of solid dosages forms like tablets, and especially orodispersible tablets.

CONTEXT OF THE INVENTION

Oil soluble substances commonly are delivered in the form oily compositions entrapped into soft capsules. However, this technique has the drawback of being expensive, labor intensive and requires specialized equipment in order to get both satisfying formulation and satisfying process. Moreover, these formulations have short shelf life.

Dry powder mixes on the contrary have longer shelf life as compared to oils, owing to their higher chemical and physical stability. Great alternative would thus to be able to formulate oily substances into the form of powder (solid dispersion) compositions. Moreover, powders are an efficient means for improving the dissolution rate and hence the bioavailability of hydrophobic drugs.

To this end, it has been recently proposed to make use of electrostatic-spray-drying techniques in order to formulate oily substances into powders. As compared to classical spray-drying, this technique has the advantage of being carried out at low temperature, thus avoiding the degradation of heat-sensitive substances. Moreover, electrostatic spray-drying is run under inert gas, thus protecting the formulation from oxidation.

This is the subject of patent application WO 2016/123224, which describes a process in which oily substances are formulated by electrostatic spray-drying. WO 2016/123224 offers a process comprising a step of emulsifying a core material with a solution or suspension of a wall material, wherein the emulsion has solids content of 15-50% by weight, and then atomizing this emulsion by electrostatic spray-drying. The core material might be selected for instance from carbohydrates, proteins, gums, lipids, waxes, food grade polymers and cellulosic materials.

However, the emulsions of WO 2016/123224 still needed to be improved, in order to obtain powders with satisfying properties.

OBJECT OF THE INVENTION

It was thus an object on the present invention to provide improved formulations of oily substances. More specifically, it was an object of the present invention to provide powders of oily substances suitable for use in solid dosage forms like tablets, in particular in orodispersible tablets.

PRESENTATION OF THE INVENTION

The inventors succeeded in improving previous formulations by developing a new emulsion formula, particularly suitable for processing oil soluble active substances by electrostatic spray-drying. The formulation comprises two different starchy materials that are an octenyl succinate starch and a maltodextrin, in particular a maltodextrin derived from amylose-rich starch.

The powder obtained thereof is directly compressible, and can thus advantageously be used for the manufacture of tablets. Moreover, the powder obtained thereof exhibits great chemical and physical stability (oxidation, photostability, temperature etc.)

Although patent application WO 2016/123224 gives a list of potential material that can be used as a wall material among which various starchy materials are cited, WO 2016/123224 never discloses nor suggest combining them. More specifically, WO 2016/123224 never disclose nor suggest combining octenyl succinate starch with a maltodextrin, in particular an amylose-rich maltodextrin.

Without being bond by any theory, the inventors believe that the two starchy materials used in accordance with the invention do not act in the same way in the oil-in-water emulsion. Contrary to the octenyl-succinate starch that is likely at the interface between the aqueous and oily phases (acting as a surface-active agent), the maltodextrin is part of the aqueous phase.

This provides advantageous properties to the powder obtained, in particular for use in tableting, and more specifically for orodispersible tablets.

BRIEF DESCRIPTION OF THE INVENTION

The invention thus first relates to a process for the preparation of a powder by electrostatic spray-drying of an oil-in-water emulsion, wherein said oil-in-water emulsion comprises an octenyl succinate starch and a maltodextrin. The invention further relates to a powder obtainable from the process of the invention. The invention further relates to a solid dosage form comprising the powder of the invention.

DETAILED DESCRIPTION OF THE INVENTION

A first object of the present invention is a process for the preparation of a powder by electrostatic spray-drying of an oil-in-water emulsion, wherein the oil-in-water emulsion comprises an octenyl succinate starch and a maltodextrin.

The octenyl succinate starch and maltodextrin useful of the invention both are starchy materials. The expression "starchy material" classically refers to a substance obtained from starch. It is reminded that the expression "starch" classically refers to the starch isolated from any suitable botanical source, by any technique well known to those skilled in the art. Isolated starch typically contains no more than 3% of impurities; said percentage being expressed in dry weight of impurities with respect to the total dry weight of isolated starch. These impurities typically comprise proteins, colloidal matters and fibrous residues. Suitable botanical source includes for instance legumes, cereals, and tubers.

The first starchy material useful to the invention is an octenyl succinate starch.

Such octenyl succinate starches are well known to those skilled in the art. They are in particular and advantageously food-grade octenyl succinate starches. Such octenyl succinate starches typically are obtainable by esterification, for instance from the reaction of a starchy material with octenyl succinic anhydride.

Preferably, the octenyl succinate starch useful to the invention is cold-water soluble. In particular, this means that the typical insoluble granular structure observed in raw starch is lost in the octenyl succinate starch. This can for instance be done by subjecting the starchy material to a so-called step of cooking. This can for instance be performed on the raw starch, before the step of esterification.

Preferably, the octenyl succinate starch useful to the invention is further partially hydrolyzed.

Preferably, the octenyl succinate starch useful to the invention is derived from starch comprising more than 50% of amylopectin, expressed as dry weight relative to the total dry weight of said starch. This amylopectin content can be classically determined by the person skilled in the art by way of potentiometric analysis of iodine absorbed by amylose to form a complex. Preferably, the octenyl succinate starch useful to the invention is derived from starch exhibiting an amylopectin content of at least 60%, still preferably of at least 80%, still preferably of at least 90%, still preferably of at least 95%.

Preferably, the octenyl succinate starch useful to the invention is derived from waxy starch, even more preferably from waxy maize starch.

Preferably, the octenyl succinate starch useful to the invention is sodium octenyl succinate starch.

Preferably, the octenyl succinate starch useful to the invention has a Hydrophilic-Lipophilic Balance (HLB), as determined by Griffin's method, selected within the range of from 8 to 16. It is preferably of at least 10, still preferably selected within the range of from 12 to 16, still preferably selected within the range of from 14 to 16, for instance equal to 15.

Preferably, the octenyl succinate starch useful to the invention has a Brookfield viscosity selected within the range of from 50 to 300 cps; said viscosity being determined on a solution comprising 24% dry weight of said octenyl succinate starch with respect to the total weight of the solution, at 20° C., after 20 min at 60 rpm using a SC4-18 spindle. Still preferably, this viscosity is selected within the range of from 90 to 150 cps.

The octenyl succinate starch useful to the invention might undergo other chemical and/or physical modification than the preferred ones exposed before, as long as it does not interfere with the desired properties, notably in term of safety and efficiency of the final powder. However, and because it appears that it is not necessary in the present invention, the octenyl succinate starch of the invention is preferably no further modified.

As example of suitable octenyl succinate starch commercially available, mention may be made of the one marketed under the name CLEARGUM® CO01 or CLEARGUM® CO03 (ROQUETTE).

The second starchy material useful to the invention is a maltodextrin. Referring to the regulatory status, maltodextrins have a dextrose equivalent (DE) of 1 to 20. Preferably, the maltodextrin useful to the invention has a DE selected within the range of from 5 to 20, preferably of from 10 to 20, preferably of from 15 to 20, for instance equal to 17.

Maltodextrins are classically cold-water soluble. They are classically obtained by enzymatic hydrolysis of a starchy paste. Attention shall be paid to the fact that maltodextrins are different from pyrodextrins (also commonly simply called "dextrins"), the latter being rather obtained by the action of heat and chemical agents on a starch powder. As a results, the molecules structure of the starchy material is different, notably with respect to the glucosidic bonds profile.

Preferably, the maltodextrin useful to the invention is derived from starch comprising at least 20% of amylose, expressed as dry weight relative to the total dry weight of said starch. This amylose content can be classically determined by the person skilled in the art by way of potentiometric analysis of iodine absorbed by amylose to form a complex. Preferably, the maltodextrin useful to invention is derived from starch exhibiting an amylose content selected within the range of from 25 to 50%, preferably of from 25 to 45%, still preferably of from 30 to 45%, still preferably of from 35 to 45%.

Preferably, the maltodextrin useful to the invention is derived from legume starch, still preferably from pea starch, still preferably from smooth pea starch.

Preferably, the maltodextrin useful to the invention has a weight average molecular weight selected within the range of from 5 000 to 15 000 Daltons (Da), preferably of from 10 000 to 15 000 Da, still preferably of from 10 000 to 14 000 Da, for instance equal to 12 000 Da. This weight average molecular can in particular be determined by the person skilled in the art by liquid chromatography with detection by differential refractometer, preferably by using pullulan standards.

The maltodextrin useful to the invention might undergo other chemical and/or physical modification than the preferred ones exposed before, as long as it does not interfere with the desired properties, notably in term of safety and efficiency of the final powder. However, and because it appears that it is not necessary in the present invention, the maltodextrin useful to the invention is preferably no further modified.

As example of suitable maltodextrin commercially available, mention may be made of the one marketed under the name KLEPTOSE® Linecaps (ROQUETTE).

Preferably the weight ratio of octenyl succinate starch to maltodextrin of the oil-in-water emulsion of the invention is selected within the range of from 1:1 to 1:100, still preferably of from 1:2 to 1:50, still preferably of from 1:5 to 1:40, still preferably of from 1:10 to 1:30, still preferably of from 1:15 to 1:25.

The oily phase of the oil-in-water emulsion of the invention is composed of an oil, in which oil-soluble substances might be further solubilized.

Examples of oils useful to the invention are animal or vegetable oils, for instance castor oil, soybean oil, palm oil, coconut oil, corn oil, cottonseed oil, olive oil, canola oil, safflower oil, sesame oil, palm kernel oil, sunflower oil, peanut oil, and combinations thereof. Preferably, the oil useful to the invention comprises (or is) corn oil.

The expression "oil-soluble substances" classically encompasses substances which are very to sparingly soluble in oil, at room temperature (20° C.). This typically means that 1 to 100 ml of oil are required in order to dissolve 1 g of said substance (International Pharmacopeia 2017, "General Notices", "Solubility"). Preferably, the oil-soluble substances of the invention are very soluble, freely soluble or soluble in oil. That is to say that 1 to 30 ml of oil are required in order to dissolve 1 g of said substance.

Preferably, the oily phase comprises an active. The active can be the oil itself, and/or an oil-soluble substance contained in it. The expression "active" classically refers to a substance having food, pharmaceutical, veterinary, nutraceutical, or cosmetic interest. Other examples of actives are substances of chemical or agrochemical interest. Preferably, the actives useful to the invention are pharmaceutical, veterinary, nutraceutical, food or cosmetic actives, in particular intended for oral administration. Suitable actives can be selected for instance selected among phenolic compounds, extracts from plant, animals or microorganisms like essential oils, antineoplastic agents, benzylphenylurea compounds, steroidal compounds, antiviral agents, antifungal agents, antitubercular agents, and anti-inflammatory agents such as ibuprofen, colorants, such as carotenoids, vitamins, such as vitamin A, vitamin E, vitamin D, and vitamin K, or from mixtures thereof. Preferably, the actives of the invention comprise (or are) oil-soluble vitamins, still preferably vitamin D, still preferably vitamin D3.

Preferably, the viscosity of the oil-in-water emulsion to be spray-dried, is selected within the range of from 10 to 500 cps, still preferably of from 50 to 200 cps, still preferably of from 90 to 150 cps; said viscosity being measured at room temperature (20-25° C.).

Preferably the solid content of the oil-in-water emulsion useful to the invention is selected within the range of from 20 to 80%, still preferably of from 30 to 70%, still preferably of from 40 to 60%, still preferably of from 50 to 55%; this percentage corresponding to the weight of solids, with respect to the total weight of said oil-in-water emulsion. It is understood that the expression "solids" refer to the substances of the oil-in-water emulsion other than the aqueous solvents, in particular other than water. The solids notably include the starchy materials and the oily phase.

Preferably, the oily phase of the oil-in-water emulsion useful to the invention represents from 1 to 50% by weight the total solid content of said oil-in-water emulsion, still preferably from 5 to 40%, still preferably from 10 to 30%.

Preferably, the starchy materials of the oil-in-water emulsion useful to the invention represent at least 40% by weight the total solid content of said oil-in-water emulsion, still preferably at least 50%, still preferably at least 60%, for instance from 70 to 90%, preferably from 70 to 85%.

For performing electrostatic spray-drying, the person skilled in the art can refer to previously mentioned patent application WO 2016/123224, describing suitable conditions for carrying out such process.

The invention further relates to a powder obtainable from the process according to the invention.

Preferably, the powder according to the invention exhibits a moisture content by weight lower than 10.0%, still preferably lower than 7.0%, still preferably lower than 5.0%.

Preferably, the powder according to the invention has a bulk density of at least 0.30 g/ml, still preferably selected within the range of from 0.30 to 0.70 g/ml, still preferably of from 0.40 to 0.60 g/ml. Preferably, the powder according to the invention has a tapped density of at least 0.30 g/ml, still preferably selected within the range of from 0.30 to 0.70 g/ml, still preferably of from 0.40 to 0.60 g/ml. These bulk and tapped densities can typically be determined by the person skilled in the art according to USP II method as in force in Oct. 1, 2017, for instance according to the method described in the working examples.

Preferably, the powder according to the invention has Carr's index lower than 15%, in particular selected within the range of from 5 to 15%, preferably, lower than 12%, still preferably lower than 10%. In other words, the powder according to the invention has excellent flowability. It is reminded that the Carr's index (C) is a well known parameter in the field of powder characterization and that it is calculated as follows:

$$C = 100 \times \frac{V_B - V_T}{V_B}$$

where
$V_B$ is the volume that a given mass of powder would occupy if let settled freely, and
$V_T$ is the volume of the same mass of powder would occupy after "tapping down".
It can also be expressed as:

$$C = 100 \times 1 - \frac{\rho_B}{\rho_T}$$

where
$\rho_B$ is the bulk density of the powder, and
$\rho_T$ is the tapped density of the powder.

Preferably, the powder according to the invention has true density selected within the range of from 1.0 to 2.0 g/cm³, still preferably of from 1.3 to 1.8 g/cm³, still preferably of from 1.4 to 1.7 g/cm³, still preferably of from 1.5 to 1.6 g/cm³. This true density can typically be determined by the person skilled in the art by way of helium pycnometer, at 25±2° C., for instance according to the method described in the working examples.

The emulsion and powder of the invention may comprise other ingredients than the ones discussed above, as long as it does not interfere with the desired propertied of the powder obtained, in particular in terms of safety and performances. Example of such ingredients are fillers like mannitol, dextrose, maltitol, xylitol, lubricants, surfactants, flavors, sweetener, and colors.

The instant invention further relates to a solid dosage form comprising the powder of the invention, preferably intended for oral administration. Preferably, the solid dosage form is selected from a powdery composition, a tablet, or a hard capsule.

In the case of powdery compositions, the later can be packed in any suitable packaging, for instance sachets or straws (for instance LifeTop™ Straw). In the case of hard capsules, the powder typically is included into the fill material of the hard capsules. For use in tablets, the powder typically is compressed.

Preferably, the solid dosage form is a fast-dissolving solid dosage form, in particular an orodispersible solid dosage form. More specifically, the solid dosage forms of the invention, in particular the tablets of the invention, preferably exhibits a disintegration time lower than 90 seconds, still preferably lower than 80 seconds, still preferably lower than 70 seconds, still preferably lower than 60 seconds, for instance from 10 to 60 seconds. This disintegration might be determined by the person skilled in the art according to US Pharmacopeia of reference "General Methods, Disintegration <701>", as in force in Oct. 1, 2017.

Preferably, the tablets of the invention have friability lower than 0.80, still preferably lower than 0.70, still preferably lower than 0.60, still preferably lower than 0.50. This friability might be determined by the person skilled in the art according to US Pharmacopeia of reference "General Chapters; Tablet Friability <1216>", as in force in Oct. 1, 2017.

The solid dosage forms of the invention may comprise other compounds than the powder of the invention, as long as it does not interfere with the desired properties, notably in terms of safety and advantageous properties of the solid dosage form. Such other possible compounds are well known to those skilled in the art, and are typically chosen according to the solid dosage form considered. Examples of such other compounds are lubricants, glidants, (super)disintegrants, binders, flavors, sweetener, and colors.

For instance, in the case of tablets, in particular of fast-dissolving tablets, the latter typically further comprise a lubricant, preferably magnesium stearate.

In a preferred embodiment, the solid dosage form of the invention, in particular the tablet of the invention, in particular the fast-dissolving tablet of the invention comprises a filler, preferably selected from binders and/or (super) disintegrants. The binders typically are intended to provide hardness to the tablets, whereas the (super)disintegrants typically provide fast-dissolving properties. Still preferably, the filler of this invention comprises (or is) a bi-functional filler, i.e. a filler with disintegrating and binding properties. Example of bi-functional fillers particularly useful to the invention are compounds of co-processed mannitol and starch, for instance like the one marketed under the name PEARLITOL® Flash (ROQUETTE) or of co-processed lactose and starch, for instance like the one marketed under the name STARLAC® (ROQUETTE).

EXAMPLES

1. Preparation of a Powder According to the Invention

In this trial, the inventors formulated an oily composition of Vitamin D3 into a powder using electrostatic spray-drying.

Vitamin D3 solubilized in corn oil at 1 million IU/g and a viscosity of 50 cps at 22° C. (Rapid Visco Analyzer by Perten Instruments) was incorporated in an oil-in-water emulsion using KLEPTOSE® Linecaps and CLEARGUM® CO01. A stable oil-in-water emulsion of Vitamin D3/KLEPTOSE® Linecaps/CLEARGUM® CO01 was prepared by high speed homogenization (using IKA mixer) followed by high pressure homogenization (Danfuss), at approx. 4500 rpm.

The formulation and characteristics of the emulsion were the following:

| | |
|---|---|
| Oily substances (Vitamin D3 solubilized in corn oil at 1 million IU/g) | 11 g |
| Maltodextrin (Maltodextrin with a DE of 17, derived from pea starch having 30-45% amylose (KLEPTOSE ® Linecaps)) | 39.6 g |
| Octenylsuccinate starch (Sodium octenyl succinate starch derived from waxy maize starch with Brookfield viscosity of 90-150 cps (CLEARGUM ® CO01)) | 2 g |
| Water | 47.4 g |
| Viscosity | 110 cps |
| Solid content | 52.6% |

The resulting emulsion was atomized through the electrostatic spray nozzle with atomizing gas pressure at 25 psi into a drying chamber. The electrostatic nozzle was applied with 20 kilo-volt (kV) charge to the starch hydration. Inside the drying chamber, drying gas (90° C.) was delivered at 25 scfm to assist water evaporation. The drying gas that applies in this technology is a mixture of air and nitrogen gas to control the oxygen level below 5% in order to minimize oxidation. A powder of 212,000 IU/g Vitamin D3 was obtained.

2. Characterization of the Powder of the Invention

Two different batches of the powder obtained according to section 1. were evaluated for moisture content, bulk density, tapped density, compressibility and flowability. Primary particle size distribution (before agglomeration) was also evaluated.

More specifically, the primary particle size distribution, and average particle diameters D3,2 and D4,3 of the primary particles were measured by particle sizer with zeta potential (Malvern). The true density was determined in triplicate by helium pycnometer (AccuPyc 1330, MicroMeritics, US) at 25±2° C. Bulk density of the final powder was determined in triplicate by adding accurately weighed (about 4 g) powder to 25 mL graduated measuring cylinder. Corresponding volume was measured to obtain the bulk density. Tapped density of the final powder was determined, as per USP II method, using automatic tapper (Stay 2003, Stampfvolumeter, Switzerland). Flowability of the final powder was determined by calculating Carr's index.

The results obtained are presented in Table 1.

TABLE 1

| | | Sample 1 | Sample 2 |
|---|---|---|---|
| Moisture content | % | 4.59 | 4.66 |
| Primary particle granulometry: | d(0.1) | 9 | 9 |
| | d(0.2) | 13 | 14 |
| Particle size | d(0.5) | 29 | 30 |
| distribution (µm) | d(0.8) | 62 | 71 |
| | d(0.9) | 99 | 141 |
| D [3, 2] - Surface weighted mean | µm | 20 | 21 |
| D [4, 3] - Volume weighted mean | µm | 70 | 114 |
| True density | g/cm$^3$ | 1.55 | 1.55 |
| Bulk density | g/ml | 0.52 | 0.50 |
| Tapped density | g/ml | 0.56 | 0.55 |
| Carr's index | % | 8 | 9.5 |
| Flowability | | Excellent | Excellent |

3. Tableting of the Powder According to the Invention

The powders of the invention were then evaluated for their tableting properties. To this end, the powders were formed into tablets of 400 mg at 1,000 IU vitamin D3 (tablets "IN-1,000 IU" according to the invention), or at 10,000 IU vitamin D3 (tablets "IN-10,000 IU" according to the invention) by way of a single punch machine (Korsh XP1) and evaluated for hardness, friability and disintegration.

The formulation of the tablets was the followings:

| | |
|---|---|
| Powder to be evaluated | 50 mg |
| Bifunctional filler (with disintegrating and binding properties) (PEARLITOL ® Flash, a compound of co-processed mannitol and starch) | 344 mg |
| Lubricant (Magnesium stearate) | 4.8 mg |
| Sweetener (Sucralose) | 1.2 mg |
| Total | 400 mg |

Friability was measured according to US Pharmacopeia of reference "General Chapters; Tablet Friability <1216>", as in force in Oct. 1, 2017. Disintegration was measured according to US Pharmacopeia of reference "General Methods, Disintegration <701>", as in force in Oct. 1, 2017.

As a comparison, commercial tablets of vitamin D3 at 1,000 IU vitamin D3 were also evaluated (comparative "CP-Commercial 1,000 IU").

The compression settings, as well as the results obtained are presented in Table 2.

TABLE 2

| Tablet reference | IN-10,000 IU | IN-1,000 IU | CP-Commercial 1,000 IU |
|---|---|---|---|
| Fc (KN) | 11.3 | 9.8 | N/A |
| Fe (N) | 86 | 111 | N/A |
| Relative Humidity | 28% | 27% | N/A |
| Hardness Average | 50.4 | 47.5 | N/A |
| Disintegration | 56 sec | 57 sec | 1 min 16 sec |
| Friability | 0.49 | 0.69 | 0.82 |

The powder according to the invention exhibits good tableting capacity, as demonstrated by its ability to form tablets of good hardness. Moreover, the tablets obtained thereof disintegrate in a short period, lower than 60 seconds, which render them suitable for use in fast-dissolving solid dosage forms, in particular for orodispersible tablets.

The invention claimed is:

1. A process for preparation of a powder by electrostatic spray-drying of an oil-in-water emulsion, wherein said oil-in-water emulsion has an oily phase comprising one or more oils selected from the group consisting of corn oil, castor oil, soybean oil, palm oil, coconut oil, cottonseed oil, olive oil, canola oil, safflower oil, sesame oil, palm kernel oil, sunflower oil, peanut oil, and combinations thereof, and wherein said oil-in-water emulsion comprises an octenyl succinate starch and a maltodextrin in a weight ratio of octenyl succinate starch to maltodextrin selected within a range of from 1:10 to 1:40,
and wherein the powder has:
a bulk density of at least 0.30 g/ml,
a tapped density of at least 0.30 g/ml, and
a Carr's index lower than 15%, wherein the Carr's index (C) is calculated as follows:

$$C = 100 \times \left(1 - \frac{\rho_B}{\rho_T}\right)$$

wherein
$\rho_B$ is the bulk density of the powder, and
$\rho_B$ is the tapped density of the powder.

2. The process of claim 1, wherein said maltodextrin is derived from starch having at least 20% of amylose, expressed as dry weight relative to the total dry weight of said starch.

3. The process according to claim 1, wherein said maltodextrin is derived from legume starch.

4. The process according to claim 1, wherein said octenyl succinate starch is derived from starch having more than 50% of amylopectin, expressed as dry weight relative to the total dry weight of said starch.

5. The process according to claim 1, wherein said octenyl succinate starch is sodium octenyl succinate starch.

6. The process according to claim 1, wherein said octenyl succinate starch has a Hydrophilic-Lipophilic Balance (HLB) selected within a range of from 8 to 16.

7. The process according to claim 1, wherein said oil-in-water emulsion exhibits a weight ratio of the octenyl succinate starch to the maltodextrin selected within a range of from 1:10 to 1:30.

8. The process according to claim 1, wherein said oil-in-water emulsion has a solid content selected within a range of from 20 to 80%, this percentage corresponding to the weight of solids, with respect to the total weight of said oil-in-water emulsion.

9. The process according to claim 1, wherein the oily phase of said oil-in-water emulsion represents from 1 to 50% by weight of the total solid content of said oil-in-water emulsion.

10. The process according to claim 1, wherein said octenyl succinate starch and said maltodextrin of said oil-in-water emulsion represent at least 40% by weight of the total solid content of said oil-in-water emulsion.

11. A powder obtained by the process according to claim 1, wherein the powder comprises an octenyl succinate starch and a maltodextrin and has:
a bulk density of at least 0.30 g/ml,
a tapped density of at least 0.30 g/ml, and
a Carr's index lower than 15%, wherein the Carr's index (C) is calculated as follows:

$$C = 100 \times \left(1 - \frac{\rho_B}{\rho_T}\right)$$

wherein
$\rho_B$ is the bulk density of the powder, and
$\rho_B$ is the tapped density of the powder.

12. The powder of claim 11, wherein said powder has a bulk density selected within a range of from 0.30 to 0.70 g/ml.

13. The powder of claim 11, wherein said powder has a tapped density selected within a range of from 0.30 to 0.70 g/ml.

14. The powder of claim 11, wherein said powder has a Carr's index selected within a range of from 5 up to 15%.

15. A tablet comprising the powder of claim 11.

16. The tablet of claim 15, wherein said tablet exhibits a disintegration time lower than 90 seconds.

17. The tablet of claim 15, wherein said tablet exhibits a disintegration time lower than 80 seconds.

18. The tablet of claim 15, wherein said tablet exhibits a disintegration time lower than 70 seconds.

19. The tablet of claim 15, wherein said tablet exhibits a disintegration time lower than 60 seconds.

20. The tablet of claim 15, wherein said tablet exhibits a disintegration time from 10 to 60 seconds.

21. The powder of claim 11, wherein said powder has a bulk density selected within a range of from 0.40 to 0.60 g/ml.

22. The powder of claim 11, wherein said powder has a Carr's index lower than 12%.

23. The powder of claim 11, wherein said powder has a Carr's index lower than 10%.

24. The process according to claim 1, wherein said oil-in-water emulsion has an oily phase comprising an oil in which oil-soluble substances can be further solubilized and an active that can be the oil itself and/or the oil-soluble substance solubilized in said oil, wherein said oily phase of said oil-in-water emulsion comprises an active that is said one or more oils itself and/or an oil-soluble substance solubilized in said one or more oils.

25. The process according to claim 24, wherein the oil-soluble substance is selected from phenolic compounds, extracts from plant, animals or microorganisms, essential oils, antineoplastic agents, benzylphenylurea compounds, steroidal compounds, antiviral agents, antifungal agents, antitubercular agents, anti-inflammatory agents, colorants, or vitamins.

26. A process for preparation of a tablet, comprising preparing the powder according to the process of claim 1, and compressing the powder.

27. The process of claim 1, wherein said maltodextrin is derived from starch having from 25 to 50% of amylose; expressed as dry weight relative to the total dry weight of said starch.

28. The process of claim 1, wherein said maltodextrin is derived from starch having from 25 to 45% of amylose; expressed as dry weight relative to the total dry weight of said starch.

29. The process of claim 1, wherein said maltodextrin is derived from starch having from 30 to 45% of amylose; expressed as dry weight relative to the total dry weight of said starch.

30. The process of claim 1, wherein said maltodextrin is derived from starch having from 35 to 45% of amylose; expressed as dry weight relative to the total dry weight of said starch.

31. The process according to claim 1, wherein said octenyl succinate starch is derived from starch having at least 60% of amylopectin; expressed as dry weight relative to the total dry weight of said starch.

32. The process according to claim 1, wherein said octenyl succinate starch is derived from starch having at least 80% of amylopectin; expressed as dry weight relative to the total dry weight of said starch.

33. The process according to claim 1, wherein said octenyl succinate starch is derived from starch having at least 90% of amylopectin; expressed as dry weight relative to the total dry weight of said starch.

34. The process according to claim 1, wherein said octenyl succinate starch is derived from starch having at least 95% of amylopectin; expressed as dry weight relative to the total dry weight of said starch.

35. The process according to claim 1, wherein said octenyl succinate starch has a Hydrophilic-Lipophilic Balance (HLB) selected within a range of at least 10.

36. The process according to claim 1, wherein said octenyl succinate starch has a Hydrophilic-Lipophilic Balance (HLB) selected within a range of from 12 to 16.

37. The process according to claim 1, wherein said octenyl succinate starch has a Hydrophilic-Lipophilic Balance (HLB) selected within a range of from 14 to 16.

38. The process according to claim 1, wherein said octenyl succinate starch has a Hydrophilic-Lipophilic Balance (HLB) equal to 15.

39. The process according to claim 1 wherein said oil-in-water emulsion exhibits a weight ratio of the octenyl succinate starch to the maltodextrin selected within a range of from 1:15 to 1:25.

40. The process according to claim 1, wherein the oily phase of said oil-in-water emulsion represents from 5 to 40% by weight of the total solid content of said oil-in-water emulsion.

41. The process according to claim 1, wherein the oily phase of said oil-in-water emulsion represents from 10 to 30% by weight of the total solid content of said oil-in-water emulsion.

42. The process according to claim 1, wherein said octenyl succinate starch and said maltodextrin of said oil-in-water emulsion represent at least 50% by weight of the total solid content of said oil-in-water emulsion.

43. The process according to claim 1, wherein said octenyl succinate starch and said maltodextrin of said oil-in-water emulsion represent at least 60% by weight of the total solid content of said oil-in-water emulsion.

44. The process according to claim 1, wherein said octenyl succinate starch and said maltodextrin of said oil-in-water emulsion represent from 70 to 90% by weight of the total solid content of said oil-in-water emulsion.

45. The process according to claim 1, wherein said octenyl succinate starch and said maltodextrin of said oil-in-water emulsion represent from 70 to 85% by weight of the total solid content of said oil-in-water emulsion.

* * * * *